US008551762B2

(12) United States Patent
Fleming et al.

(10) Patent No.: US 8,551,762 B2
(45) Date of Patent: Oct. 8, 2013

(54) SYSTEM AND APPARATUS FOR FEEDING, SOLUBILIZING, GROWING AND DISCHARGING A BIOLOGICAL MATERIAL

(75) Inventors: Wayne Anthony Fleming, Dallas, TX (US); William Pierre Boesch-Deveze, Plano, TX (US); Jose Eduardo G. Evaro, Mansfield, TX (US); Robert Clarence Pearce, III, Arlington, TX (US); Michael Eugene Rushing, Denton, TX (US); Michael Joseph Trevino, Bedford, TX (US)

(73) Assignee: NCH Corporation, Irving, TX (US)

( * ) Notice: Subject to any disclaimer, the term of this patent is extended or adjusted under 35 U.S.C. 154(b) by 672 days.

(21) Appl. No.: 12/571,714

(22) Filed: Oct. 1, 2009

(65) Prior Publication Data
US 2011/0081713 A1 Apr. 7, 2011

Related U.S. Application Data

(63) Continuation-in-part of application No. 12/498,793, filed on Jul. 7, 2009.

(51) Int. Cl.
*C12M 1/36* (2006.01)
*C12M 1/02* (2006.01)
*B01J 8/10* (2006.01)
*B01F 15/04* (2006.01)
*G01F 11/20* (2006.01)

(52) U.S. Cl.
USPC ............... 435/286.5; 435/286.7; 435/289.1; 422/261; 366/162.2; 222/325; 222/368

(58) Field of Classification Search
USPC .............. 435/286.5, 286.7, 289.1; 422/261
See application file for complete search history.

(56) References Cited

U.S. PATENT DOCUMENTS

| | | | |
|---|---|---|---|
| 3,055,856 A | 9/1962 | Sutherland | |
| 3,152,983 A | 10/1964 | Davis et al. | |
| 3,220,706 A | 11/1965 | Valdespino | |
| 3,242,055 A | 3/1966 | DeLucia | |
| 3,301,442 A * | 1/1967 | Schwertfeger et al. | 222/252 |
| 3,617,538 A | 11/1971 | Bogert | |
| 3,642,257 A | 2/1972 | Tanaka et al. | |
| 4,051,204 A | 9/1977 | Muller et al. | |
| 4,116,246 A | 9/1978 | Franzen | |
| 4,162,795 A | 7/1979 | Kanics | |
| 4,244,815 A | 1/1981 | Chaikin et al. | |
| 4,426,450 A | 1/1984 | Donofrio | |
| 4,790,981 A | 12/1988 | Mayer et al. | |
| 4,797,208 A | 1/1989 | Miller et al. | |

(Continued)

FOREIGN PATENT DOCUMENTS

| | | |
|---|---|---|
| DE | 19507456 | 3/1995 |
| EP | 0130499 | 1/1985 |

(Continued)

*Primary Examiner* — William H Beisner
(74) *Attorney, Agent, or Firm* — Monty L. Ross; Robin L. Barnes; Ross Barnes LLP

(57) ABSTRACT

Apparatus useful for feeding a particulate starter material comprising nutrient and bacteria to a mixing tank, for solubilizing the starter material inside the mixing tank, for promoting growth of the bacteria and for discharging an aqueous slurry comprising the bacteria from the mixing tank. The apparatus preferably has a gravity-flow feeder and discharge port, does not require a pump, and comprises disposable parts.

5 Claims, 5 Drawing Sheets

(56) References Cited

U.S. PATENT DOCUMENTS

| | | | |
|---|---|---|---|
| 4,810,385 A | 3/1989 | Hater et al. | |
| 4,832,848 A | 5/1989 | Velebil et al. | |
| 4,840,905 A | 6/1989 | Kearns et al. | |
| 4,883,759 A | 11/1989 | Hopkins | |
| 4,888,294 A | 12/1989 | Van Wezel et al. | |
| 4,911,832 A | 3/1990 | Miller et al. | |
| 4,925,564 A | 5/1990 | Francis | |
| 4,960,706 A | 10/1990 | Bliem et al. | |
| 5,162,204 A | 11/1992 | Matsuzaki et al. | |
| 5,225,083 A | 7/1993 | Pappas | |
| 5,232,664 A | 8/1993 | Krawzak et al. | |
| 5,251,656 A | 10/1993 | Sexton, Sr. | |
| 5,275,943 A | 1/1994 | DiTuro | |
| 5,350,543 A | 9/1994 | Spradley | |
| 5,369,032 A | 11/1994 | Pratt | |
| 5,401,501 A | 3/1995 | Pratt | |
| 5,426,024 A | 6/1995 | Flores-Cotera et al. | |
| 5,447,866 A | 9/1995 | Runyon | |
| 5,470,544 A | 11/1995 | Galloway | |
| 5,516,687 A | 5/1996 | Perez et al. | |
| 5,525,301 A | 6/1996 | Newberg et al. | |
| 5,654,197 A | 8/1997 | Jem et al. | |
| 5,716,630 A | 2/1998 | Lin et al. | |
| 5,739,031 A | 4/1998 | Runyon | |
| 5,770,079 A | 6/1998 | Haase | |
| 5,849,253 A * | 12/1998 | Crossdale et al. | 422/264 |
| 5,911,877 A | 6/1999 | Perez et al. | |
| 5,988,461 A | 11/1999 | Edney et al. | |
| 5,998,184 A | 12/1999 | Shi | |
| 6,168,949 B1 | 1/2001 | Rubenberger | |
| 6,190,591 B1 | 2/2001 | Van Lengerich | |
| 6,254,886 B1 | 7/2001 | Fusca et al. | |
| 6,280,719 B1 | 8/2001 | Suh | |
| 6,325,934 B1 | 12/2001 | Tobet, Jr. et al. | |
| 6,335,191 B1 | 1/2002 | Kiplinger et al. | |
| 6,562,585 B1 | 5/2003 | Hiatt | |
| 6,706,518 B2 * | 3/2004 | Lorenz et al. | 435/264 |
| 6,723,526 B1 | 4/2004 | Hernandez et al. | |
| 6,733,781 B2 | 5/2004 | Abu-Izza et al. | |
| 7,081,361 B2 | 7/2006 | Pearce et al. | |
| 1,618,461 A1 | 2/2007 | Matchette | |
| 7,223,075 B2 | 5/2007 | Schmitt | |
| 2005/0032032 A1 | 2/2005 | Pearce, III et al. | |
| 2005/0054086 A1 | 3/2005 | Ophardt | |
| 2005/0247742 A1 * | 11/2005 | Livingston et al. | 222/444 |
| 2007/0295755 A1 | 12/2007 | Kinzie et al. | |
| 2009/0130740 A1 | 5/2009 | Ophardt | |
| 2011/0008220 A1 * | 1/2011 | Fleming et al. | 422/261 |

FOREIGN PATENT DOCUMENTS

| | | |
|---|---|---|
| EP | 0487867 | 6/1992 |
| EP | 0381776 B1 | 4/1994 |
| FR | 2044546 | 2/1971 |
| GB | 2162195 | 1/1986 |
| GB | 2207415 A * | 2/1989 |
| JP | 03266974 | 11/1991 |
| WO | WO 02079497 | 10/2002 |
| WO | WO 03016460 | 2/2003 |

* cited by examiner

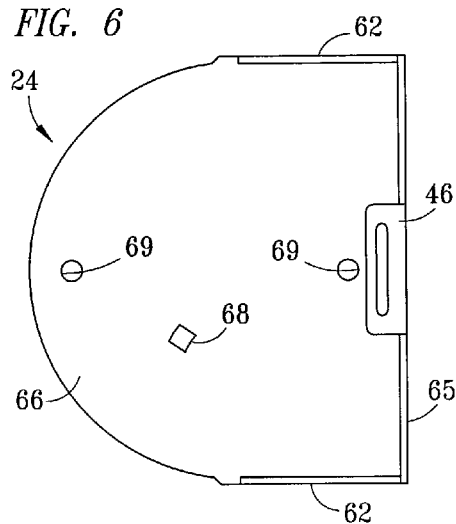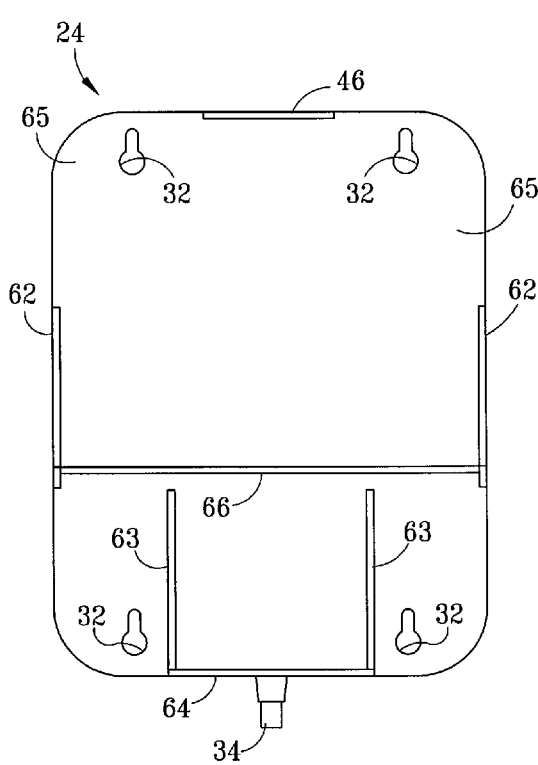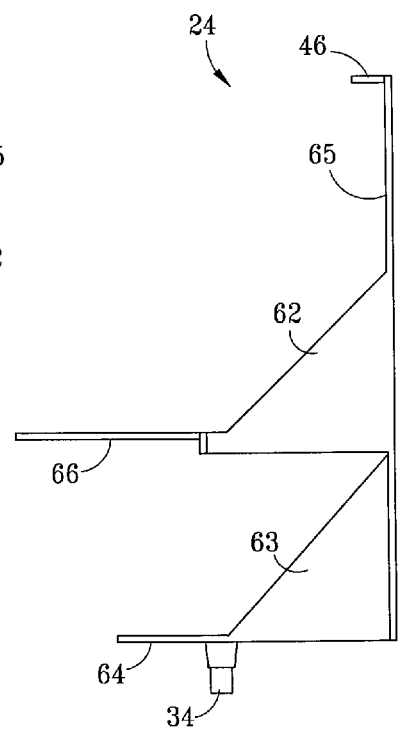

US 8,551,762 B2

SYSTEM AND APPARATUS FOR FEEDING, SOLUBILIZING, GROWING AND DISCHARGING A BIOLOGICAL MATERIAL

CROSS-REFERENCE TO RELATED APPLICATION

This application is a continuation-in-part of U.S. application Ser. No. 12/498,793, filed Jul. 7, 2009.

BACKGROUND OF THE INVENTION

1. Technical Field

This invention relates to a system and apparatus for feeding and solubilizing a solid biological starter material, and for aerating, growing and dispensing aqueous mixtures of select vegetative bacterial strains for various end use applications. Such end use applications can include, for example, digestion and removal of grease from food processing or restaurant drains, grease traps, grease interceptors and sewers, and bioremediation of other amenable wastes and waste streams. The system and apparatus of the invention preferably comprise some disposable components, principally for convenience and to reduce the time required to clean and maintain the device.

2. Related Art

Biological growth and dispensing systems with various feeder devices have previously been disclosed, for example, in U.S. Pat. Nos. 7,081,361 and 6,335,191, and in the prior art referenced in those patents, and in pending published U.S. Patent Application No. 20090130740.

Some devices previously disclosed for use in feeding tableted, prilled, pelletized, granular or powdered bacterial starter materials have encountered difficulties with bridging or jamming. Similarly, some devices previously disclosed for use in solubilizing solid starter materials in an aqueous or other liquid medium have required the use of a pump driven by an electric motor for mixing, transferring or dispensing the liquid medium. Other previously disclosed devices have required time-consuming and costly periodic cleaning to alleviate flow path blockages attributable to bacterial growth inside flow lines.

A need therefore exists for a compact and relatively inexpensive system and apparatus that can reliably feed, solubilize, transfer and dispense functionally effective amounts of solubilized and/or slurried vegetative biological material for smaller volume applications by gravity flow without requiring a pump. Such system and apparatus will desirably comprise some disposable components and will reduce or eliminate the need for periodic manual cleaning and associated downtime and expense associated with time-consuming maintenance intervals.

SUMMARY OF THE INVENTION

The system and apparatus of the invention desirably comprise a compact, wall-mounted housing with a frame and cover that support and conceal a feeder unit containing a solid starter material, a feeder drive assembly disposed beneath the feeder unit, a mixing tank that also serves as a bacteria growth vessel in which the solid starter material is solubilized, circulated and aerated to increase the bacteria population during a predetermined cycle of operation (such as 24 hours), a water supply at standard line pressure to fill, circulate and aerate the bacteria inside the mixing tank, a control system that comprises liquid flow lines, timing circuitry and solenoid valves operated by motors powered by direct current, and a direct current power supply such as a battery.

According to one preferred embodiment of the invention, the feeder unit further comprises a feed canister or hopper and a feeder base and lid assembly that includes a rotatable feeder cup. Particulate solid starter material, preferably comprising a bacterial component and a nutrient component, is desirably provided in the form of pellets, prills, tablets or granules. A plastic container in which the solid starter material is shipped can also serve as the feed canister or hopper, and becomes an integral part of the feeder unit when attached to the feeder base and lid assembly. The rotatable feeder cup can optionally further comprise anti-bridging surface enhancements and can be used in combination with an overlying pellet dam having an upwardly directed surface configured to help orient the solid feed particles so as to reduce the likelihood of bridging or jamming. In either case, the rotatable feeder cup will desirably comprise a feed chamber having an open top and bottom through which a predetermined measure of the solid feed material can fall by gravity flow as the opening passes over aligned feed ports disposed above the mixing tank. The feeder drive assembly that rotates the rotatable feeder cup preferably comprises a drive shaft and gear assembly powered by a small DC motor.

The mixing tank is preferably disposed beneath the feeder unit and is generally cylindrical with a lower section that is preferably frusto-conical and comprises a bottom drain. A rigid overflow drain tube is preferably disposed in sealing engagement with the drain and has an upwardly extending free end. The drain tube is optionally releasably engageable with the bottom wall of the mixing tank, provided that a liquid seal is provided in the area of the releasable engagement to prevent leakage. The free end of the overflow drain tube is adapted to receive and drain liquid from the vessel so as to prevent the liquid level inside the vessel from exceeding a desired maximum level that is at least one inch lower than the closest water inlet to establish the air gap required by most building codes to avoid possible contamination of potable water supplies. Water is desirably introduced into the growth vessel at the beginning of each cycle of operation, after which solid starter material is introduced into the mixing tank from the feeder unit. Throughout the cycle of operation, smaller quantities of water are again introduced into the mixing tank periodically to mix and aerate the aqueous bacterial slurry inside the tank. This is most preferably achieved by directing at least two diametrically opposed jets of the incoming water in either a clockwise or counter-clockwise direction that is substantially tangential to the outside wall of the tank.

As the cumulative liquid fill level inside the mixing tank approaches the drain level of the rigid overflow drain tube, bacteria floating at or near the top surface of the liquid are carried by the liquid into the rigid overflow drain tube and out the drain by gravity flow, preferably to intermediate storage or to a desired end-use application. Inlet scuppers are desirably provided near the top of the rigid overflow drain tube to facilitate the flow of bacterial slurry into the rigid overflow drain tube. At the end of each cycle operation and commencement of the next cycle of operation, most of the bacteria present in the mixing tank and floating near the surface is discharged through the rigid overflow drain tube by introducing a sufficient volume of new water to displace the water already present in the tank.

The control system preferably comprises a microprocessor that operates solenoid valves to control water flow to the apparatus at designated times for predetermined and preset intervals, and also activates the feeder drive assembly beneath the feeder unit at desired times and for a preset interval, thereby facilitating charging, solubilization and mixing of the solid feed material, periodic mixing and aeration of the beneficial aqueous vegetative bacterial slurry thus created, and harvesting of the bacteria during and at the end of each cycle of operation.

The particulate starter material comprising bacteria and nutrient is desirably discharged downwardly through the apparatus of the invention by gravity flow, relying only on a small direct current motor rotating the drive shaft of the feeder drive assembly to sweep a desired quantity of starter material into the mixing tank. The quantity of starter material introduced into the mixing tank is determined by the size of the feed chamber and/or the number of complete (360°) rotations of the rotatable feeder cup.

Similarly, the aqueous bacterial slurry that is produced in the subject apparatus is preferably discharged from the unit by gravity flow. Normal municipal water pressure is typically relied upon for operation of the invention, and no pump is required to circulate the water or to pump out the aqueous bacterial slurry at the conclusion of each cycle of operation. The normal line pressure is typically sufficient to introduce water into the mixing tank and to periodically pulse water through jets disposed above the liquid level in the mixing tank with sufficient force to cause the water to swirl inside the tank, thereby solubilizing the particulate starter material, aerating the water and enhancing bacterial growth.

According to another embodiment of the invention, a feeder unit for particulate solids is disclosed that comprises a feed canister, a dam disposed below the feed canister, a rotatable feeder cup disposed below the dam, and a receptacle disclosed below the rotatable feeder cup. The dam and rotatable feeder cup preferably each comprise an arcuate section having an opening through which particulate solids can flow gravitationally. The rotatable feeder cup is preferably rotatable relative to the dam. At least one, and preferably both, of the dam and the rotatable feeder cup desirably comprises upwardly facing surface enhancements that help reduce the likelihood of bridging or jamming of the particulate solids. According to a particularly preferred embodiment of the invention, the entire particulate solids feeder unit is disposable and recyclable, and is changed out during periodic servicing following use of substantially all the particulate starter material in the feed canister.

BRIEF DESCRIPTION OF THE DRAWINGS

For a more complete understanding of the present invention and for further advantages thereof, reference is now made to the following description taken in conjunction with the accompanying drawings in which:

FIG. 6 is a top plan view of a preferred housing frame for use in the apparatus of FIG. 1, rotated 90 degrees in a clockwise direction from the front elevation position as shown in FIG. 7 to a position corresponding to the top plan view of the right side elevation view of the frame as shown in FIG. 8;

FIG. 7 is a front elevation view of the frame of the FIG. 6;

FIG. 8 is a right side elevation view of the frame of FIG. 6;

Like reference numerals are used to indicate like parts in all figures of the drawings.

DESCRIPTION OF PREFERRED EMBODIMENT

Figure 1:
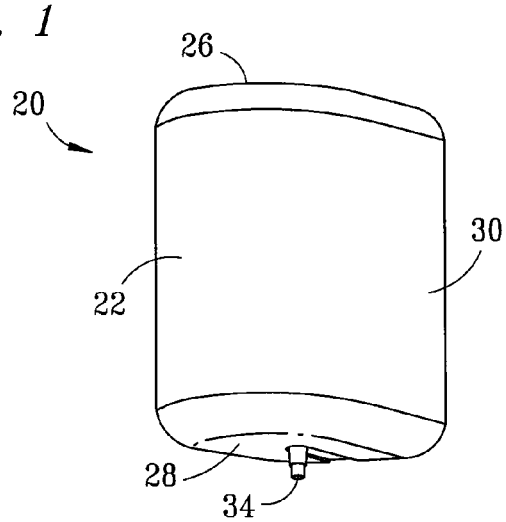
FIG. 1 is a bottom front perspective view of a preferred embodiment of an apparatus for feeding and solubilizing a solid biological starter material, and for aerating, growing and discharging aqueous slurries of select vegetative bacterial strains for various end use applications, with the housing cover in place.
Figure 2:
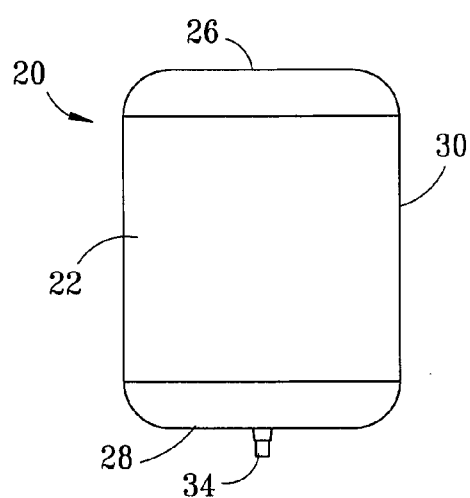
FIG. 2 is a front elevation view of the apparatus of FIG. 1.
Figure 3:
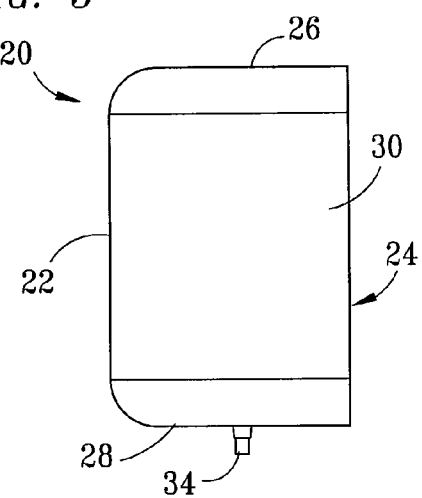
FIG. 3 is a right side elevation view of the apparatus of FIG. 1.
Figure 4:
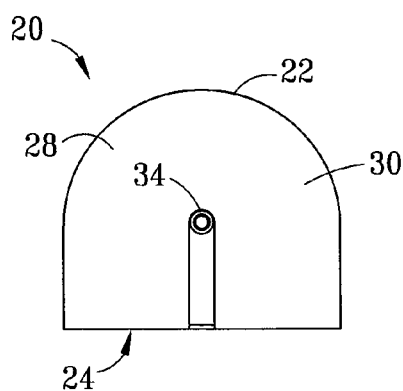
FIG. 4 is a bottom plan view of the apparatus of FIG. 1.
Figure 5:
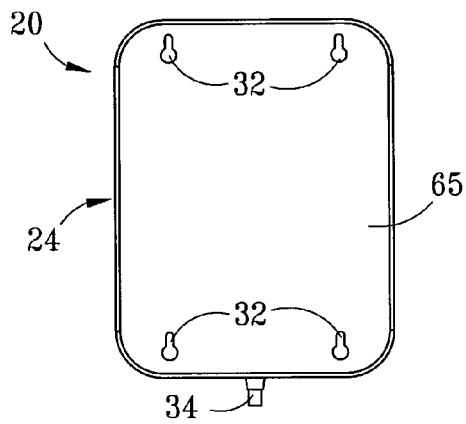
FIG. 5 is a rear elevation view of the apparatus of FIG. 1.

Referring to FIGS. 1-8, a preferred apparatus 20 of the invention preferably includes a housing having a removable cover 30 and a frame 24. Cover 30 desirably has a modern styled highly finished look and is attachable to frame 24 by frictional engagement and is preferably completely removable to facilitate access to the interior of apparatus 20. It will be understood and appreciated, however, that cover 30 can likewise be connected to frame 24 by other similarly effective means such as hinges, for example, provided that access to the interior of apparatus 20 can still be achieved. Cover 30 can also snap on or screw on and, if desired, a lock (not shown) can also be provided to control access to the interior of the housing. Cover 30 includes front, top and bottom wall sections 22, 26, 28, respectively. Extending from or through bottom 28 of cover 30 is an outlet port 34 for use in discharging aqueous bacterial slurries produced in apparatus 20. Either or both of cover 30 and frame 24 are preferably made of a suitable metal or plastic, although frame 24, if made of plastic, should be made of durable plastic that is resistant to fading, cracking, creep or other structural failure when used over prolonged periods.

Frame 24 of apparatus 20 preferably includes mounting plate 65 having apertures 32 (FIGS. 5 and 7) for insertion of mounting screws or other conventional fasteners (not shown) for mounting frame 24 and apparatus 20 to a support structure such as, for example, a wall. Frame 24 desirably further comprises upper support plate 66 and lower support plate 64, each of which is either made integrally with or connected to mounting plate 65 and bracket members 62, 63, respectively, that are preferably disposed at each side of the respective base plates and also project forwardly from mounting plate 65. Upper support plate 66 desirably includes aperture 68 for through which particulate matter passes from feeder unit 70 into mixing tank 56 and apertures 69 for use in installing circulating jets 116, 118 as described below in relation to FIGS. 17-18. Top bracket 46 is provided for use in releasably attaching cover 22 (FIG. 1) to frame 24 if desired.

Figure 16:
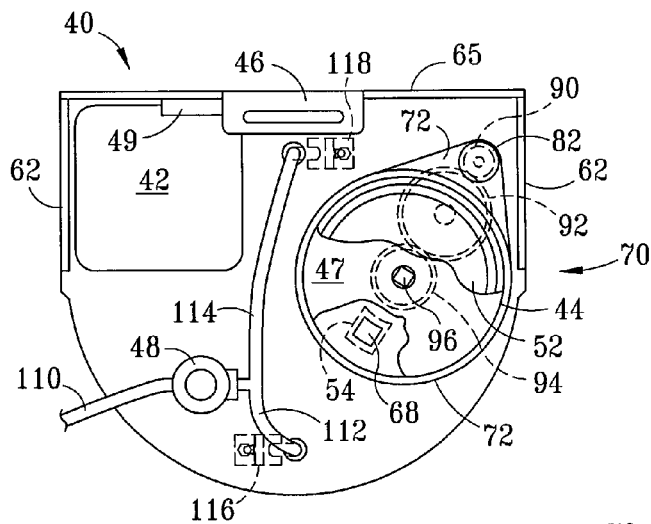
FIG. 16 is a top plan view of the apparatus of FIG. 1 with the cover removed.
Figure 17:
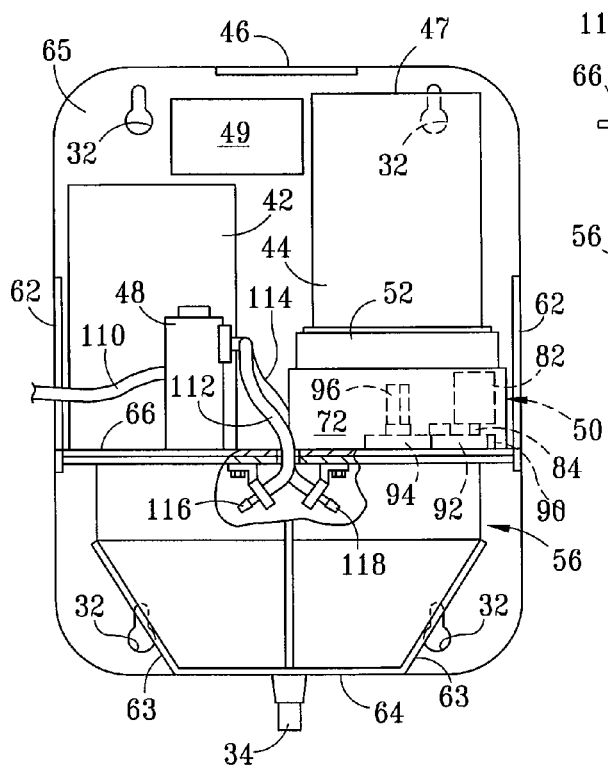
FIG. 17 is a front elevation view of the apparatus of FIG. 1 with the cover removed.
Figure 18:
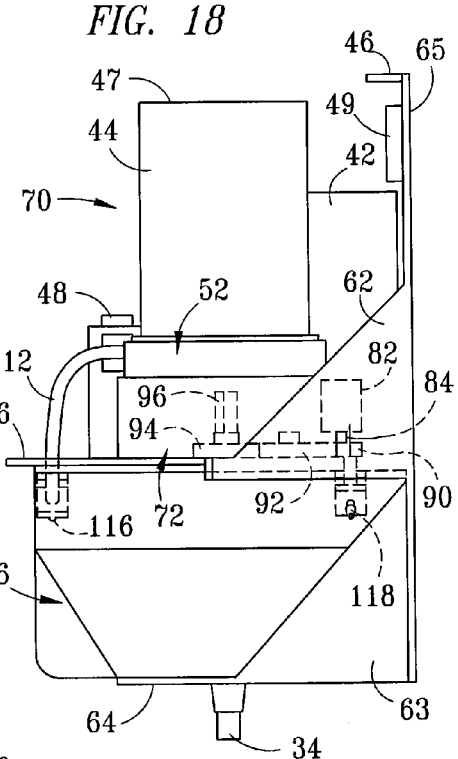
FIG. 18 is a right side elevation view of the apparatus of FIG. 1 with the cover removed.

Referring to FIGS. 16, 17 and 18, mounting plate 65 and upper and lower support plates 66, 64 facilitate attachment of, and provide mounting sites for, microprocessor 49, battery 42 or, alternatively, an alternating current power adapter (not shown), water flow lines 110, 112, 114, liquid flow control system 48, feeder unit 70, feeder drive assembly 50 and mixing tank 56. Mixing tank 56 preferably has top flanges that slide into engagement with a cooperating flange of upper support plate 66. Lower support plate 64 comprising drain port 34 desirably mates with an effluent outlet lip on the bottom side of mixing tank 56.

Figure 9:
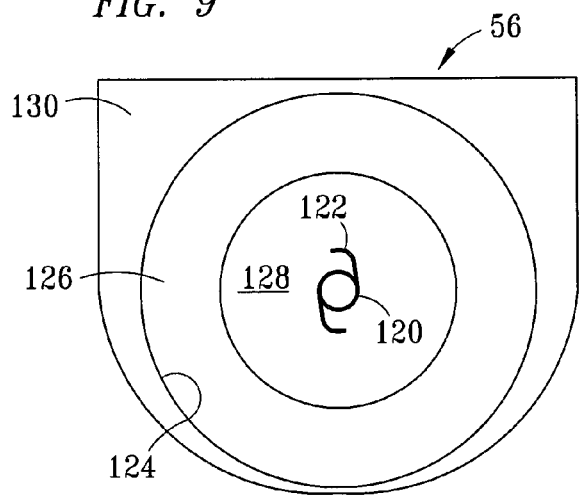
FIG. 9 is a top plan view of a preferred mixing tank and bacteria growth vessel ("mixing tank") for use in the apparatus of FIG. 1.
Figure 10:
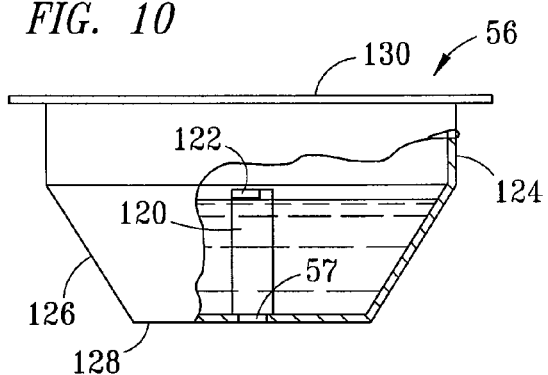
FIG. 10 is a front elevation view, partially broken away and partially in section, of the mixing tank of FIG. 9.
Figure 11:
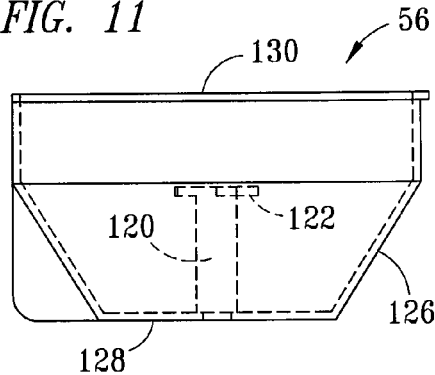
FIG. 11 is a right side elevation view of the mixing tank of FIG. 9.
Figure 12:
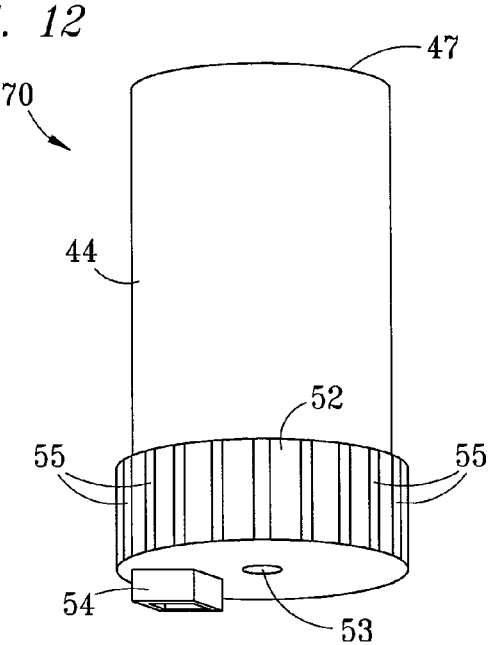
FIG. 12 is a bottom perspective view of a preferred feeder unit for use in the apparatus of FIG. 1.
Figure 13:
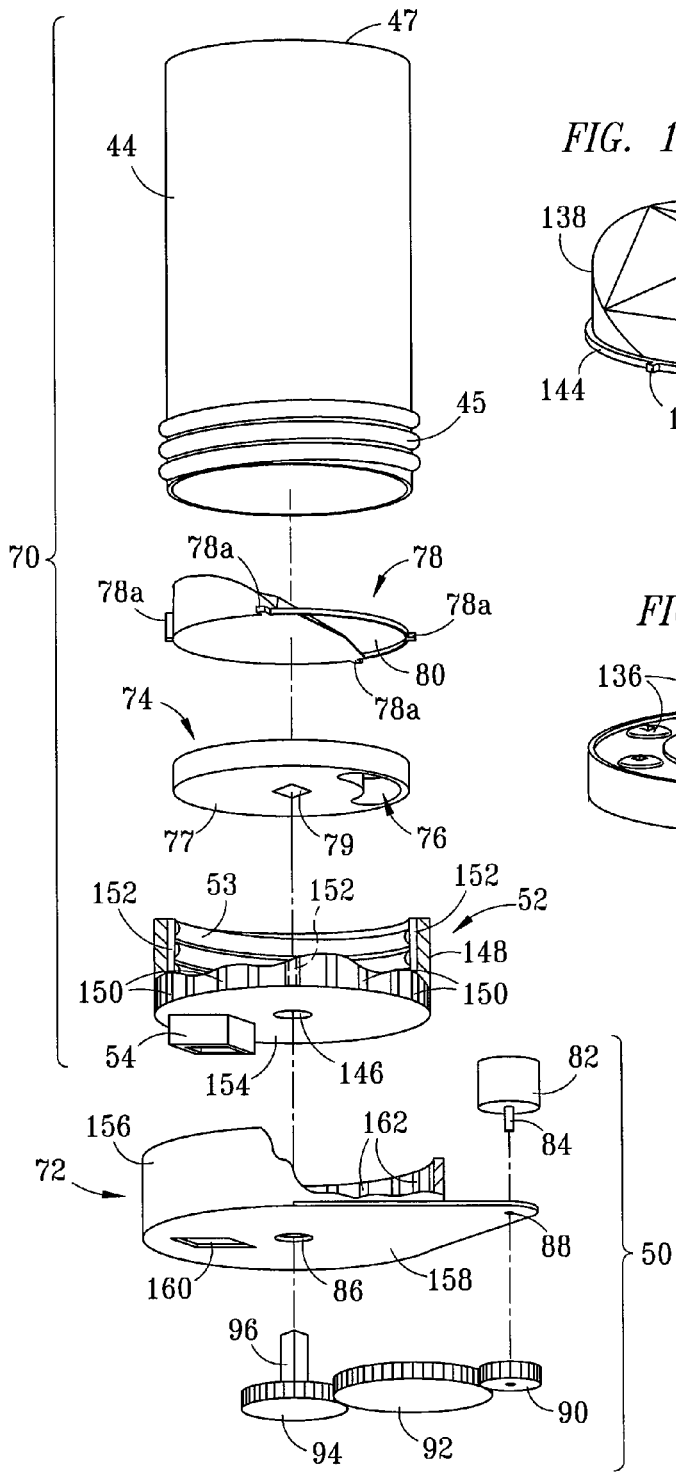
FIG. 13 is an exploded bottom perspective view of the feeder unit of FIG. 12 in combination with a preferred feeder drive assembly that activates the rotatable feeder cup.

Referring to FIGS. 9-11, mixing tank 56 can be made of a disposable and recyclable material, and preferably comprises a top flange 130 defining a substantially circular top opening, a substantially cylindrical upper wall section 124, a frusto-conical lower sidewall section 126, and bottom 128 having a centrally disposed drain port 57. Overflow drain tube 120, preferably comprising inlet scuppers 122, is provided for use in harvesting the aqueous bacterial slurry produced in the invention. The liquid capacity of mixing tank 56, which is determined by the height of overflow drain tube 120, is desirably about 750 ml in a preferred embodiment of the invention, but can vary according to other design parameters and the intended application for a particular apparatus. Bacteria slurry periodically overflow via gravity at preset timed intervals triggered by additions of cold water to the mixing tank. The liquid capacity of the mixing tank can also vary depending on the specific design of a particular apparatus intended for a particular end use application.

Referring to FIGS. 12-15, particulate matter feeder unit 70 preferably comprises inverted feed canister 44 having a solid end wall 47 and an opposed open end surrounded by threads 45. The volume of feed canister 44 is preferably sufficient to contain enough particulate feed material to last through a targeted number of operational cycles during a desired service interval. Feed canister 44 is preferably designed so that threads 45 are cooperatively engageable with threads 53 of feeder base and lid assembly 52. Pellet dam 78 and rotatable feeder cup 74 are preferably disposed inside feeder base and lid assembly 52 prior to attachment of feed canister 44 to feeder base and lid assembly 52. When constructed in this or a similarly effective configuration, feed canister 44 can be shipped preloaded with the particulate starter material, pellet dam 78 and rotatable feeder cup 74 in place and oriented so that feeder base and lid assembly 52 is attached and ready for insertion into feeder drive base 72 of feeder drive assembly 50 at the time of use. Following use for predetermined service intervals, the entire feeder unit can be disposed of for subsequent recycling, and a new feeder unit can be installed. If desired, mixing tank 56 can likewise be disposed of and another installed together with the feeder unit.

Figure 14:
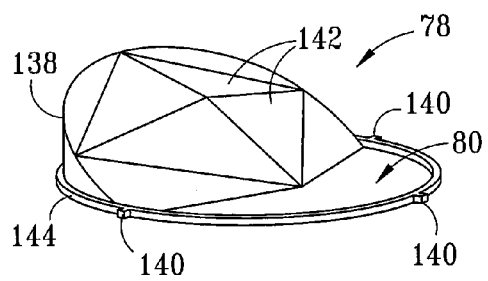
FIG. 14 is a top perspective view of a preferred embodiment of a pellet dam for use in the feeder unit of FIG. 12.
Figure 15:
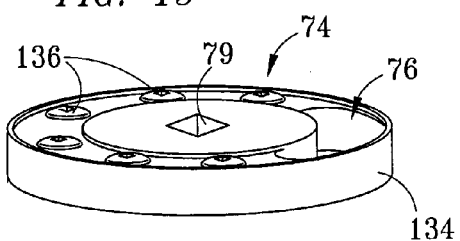
FIG. 15 is a top perspective view of a preferred embodiment of a rotatable feeder cup for use in the feeder unit of FIG. 12.

Feeder base and lid assembly 52 preferably further comprises side wall 148 having circumferentially spaced keyways 152 that receive keys 78a (shown as 140 in FIG. 14) of pellet dam 78 to prevent pellet dam from rotating relative to feeder base and lid assembly 52. Referring to FIG. 14, pellet dam 78 preferably further comprises a raised, wedge-shaped section 138 comprising surface enhancements 142 intended to help prevent the particulate feed material flowing downwardly out of feed canister 44 (FIG. 13) from bridging or jamming prior to flowing further downward by gravity flow through opening 80 inside bottom rim 144 of pellet dam 78 and through feed chamber 76 of rotatable feeder cup 74 (FIG. 15), downwardly projecting discharge port 54 of feeder base and lid assembly 52 (FIG. 13), and aperture 160 of feeder drive base 72 into mixing tank 56 (FIG. 17). Feed chamber 76 of rotatable feeder cup 74 has no top or bottom, but is disposed over a solid surface of bottom 154 of feeder base and lid assembly 52 at the time it receives particulate feed material flowing downwardly through opening 80 in pellet dam 78. As rotatable feeder cup 74 rotates between pellet dam 78 and bottom 154 of feeder base and lid assembly 52, feed chamber 76 sweeps under opening 80 and receives particulate feed sufficient to substantially fill the cup, then rotates over aperture 68 (FIG. 16) in projecting discharge port 54 in bottom 154 of feeder base and lid assembly 52 to discharge the particulate feed into mixing tank 56. Feeder cup 74 also preferably has surface enhancements 136 that contact opening 80 in pellet dam 78 when the feed chamber 76 is rotated out of alignment with the opening 80 in pellet dam 78. These surface enhancements 136 also help prevent bridging or lamming of the particulate matter.

The preferred rectangular shape of downwardly projecting discharge port 54 of feeder base and lid assembly 52 (FIG. 13) desirably releasably engages aperture 160 in bottom 158 of feeder drive base 72 and aperture 68 in upper support plate 66, preventing feeder base and lid assembly 52 from rotating relative to feeder drive base 72. Drive shaft 96 is preferably square and cooperatively sized to fit snugly inside aperture 79 of rotatable feeder cup 74 to insure that rotatable feeder cup 74 rotates with drive shaft 96. Conversely, apertures 86 of feeder drive base 72 and aperture 146 in bottom 154 of feeder base and lid assembly 52 are desirably large enough to permit drive shaft 96 to rotate freely inside them. Ribs 150 in outside wall 148 of feeder lid and base assembly 52 are sized and configured to cooperatively engage ribs 162 inside wall 156 of feeder drive base 72 to snugly hold feed canister 44 in place during use of apparatus 20 (FIG. 1).

Referring to FIGS. 13 and 15-18, feeder drive assembly 50 preferably further comprises gear assembly 90, 92, 94 driven by shaft 84 of small direct current motor 82 that is mounted through aperture 88 in bottom 158 of feeder drive base 72. This is preferably a center axle multiple gear drive with an offset motor. Rotatable feeder cup 74 preferably comprises a substantially cylindrical disk having a centrally disposed aperture 79 adapted to receive drive shaft 96 (FIG. 13) extending upwardly through coaxially aligned apertures 86 and 146 in feeder drive base 72. When motor 82 powered by battery 42 is actuated by a signal received from microprocessor 49, gear assembly 90, 92, 94 causes drive shaft 96 to rotate, thereby causing rotatable feeder cup 74 to rotate and feed particulate starter material into mixing tank 6556.

Battery 42, which is most preferably a rechargeable battery pack and/or a 110v a/c to d/c converter, supplies power to liquid flow control unit 48, d/c motor 82 for gear for feeder drive assembly 50, and microprocessor 49. Liquid flow control unit 48 desirably comprises at least one solenoid valve, and microprocessor 49 controls the cold tap water inlet solenoid cycles at designated times, thereby facilitating dissolution and mixing of the solid product in the initial operational cycle, and for mixing addition of dissolved oxygen and final dispensing of vegetative bacteria to the desired application near and at the end of the operational cycle. Microprocessor 49 also actuates motor 82 of feeder drive assembly 50 to cause feeder unit 70 to discharge particulate feed material into the water contained in mixing tank 56.

An example of microprocessor pre-set times for addition of the particulate starter material comprising bacterial and nutrient components and for water injection according to a preferred 24-hour operational cycle are as follows:

Beginning of cycle @ 0 hours, —run cold tap water for 5 min.

After this cycle, feeder unit 70 activates and discharges a predetermined weight or volume of particulate feed material to the water in the growth vessel.

Mix and aerate cycle #1 @ 6 hours—run cold tap water for 3 seconds.

Mix and aerate cycle #2 @ 12 hours—run cold tap water for 3 seconds.

Mix and aerate cycle #3 @ 16 hours—run cold tap water for 3 seconds.

Mix and aerate cycle #4 @ 19 hours—run cold tap water for 3 seconds.

Mix and aerate cycle #5 @ 22 hours—run cold tap water for 3 seconds

Return to step #1 @ 24 hours.

It should be understood that these water injection times can vary based on requirements for specific bacteria, ambient temperatures or other conditions affecting dissolved oxygen requirements.

Flow control system 48, which comprises at least one solenoid valve, controls the mix/aeration cycle as well as the 'run tap water for 5 minutes' beginning of cycle which results in the dispensing of the live vegetative bacteria into the desired application. This 'run tap water for 5 minutes' cycle also replenishes the growth vessel with clean cold tap water just prior to the addition of the solid biological product initiating the preferred 24-hour operational cycle.

Zero Jet water inlets 116, 118 mounted to or received through apertures in upper support plate 66 are preferably positioned diametrically opposite and equidistant from the geometric center of mixing tank 56, with liquid overflow tube 120 positioned at the center of that circle. Water inlets 116, 118 are positioned a minimum of 1 inch above the highest anticipated liquid level inside mixing tank 56 to comply with plumbing code regulations requiring a one-inch air gap and are preferably directed perpendicular to the intersecting horizontal diameter line on which they are positioned to induce a 'spinning' water movement which is conducive to mixing and aerating of the resulting solution/mixture. It should be understood that the number or size of jets, and the corresponding positional relations can vary provided that the objectives of enhanced dissolution, mixing and aeration are achieved so as to promote bacterial growth.

The vegetative bacteria contained in the aqueous bacterial slurry thus formed is then directed to application injection sites, e.g., floor drain, waste pit, grease trap, grease interceptor, process waste streams, municipal waste streams, and the like. Feeder driver base 72, rotating feeder cup 74, pellet dam 78 and mixing tank 56 are all disposable and recyclable components that can be replaced whenever it is necessary during normal interval maintenance to minimize cleaning.

Although particulate matter feeder unit 70 as disclosed herein is a preferred feeder unit for apparatus 20 of the invention, it should be appreciated by those of skill in the art upon reading this disclosure that feeders incorporating structural elements that are equivalent to those disclosed herein likewise have applicability to many other devices and systems in which a controllable gravitational feeder for particulate solids is desired for other applications. Accordingly, the design and use of a feeder unit similar to feeder unit 70 disclosed herein for purposes other than for growing and harvesting aqueous slurries of bacterial is also contemplated to constitute part of the subject invention in the absence of prior art disclosing same.

Other modifications and improvements to the system and apparatus disclosed herein will likewise become apparent to those of ordinary skill in the art upon reading this disclosure and it is intended that the scope of the invention be limited only by the broadest interpretation of the appended claims to which the inventors are legally entitled.

We claim:

1. Apparatus useful for feeding a particulate starter material comprising nutrient and bacteria to a mixing tank, for solubilizing the starter material inside the mixing tank, for promoting growth of the bacteria and for discharging an aqueous slurry comprising the bacteria from the mixing tank, the apparatus comprising:
    a housing having a frame and a releasable cover;
    a particulate matter feeder unit;
    a feeder drive assembly supported by the frame and releasably engaged with the particulate matter feeder unit to allow dispensing of particulate starter material;
    a liquid flow control system;
    a mixing tank disposed at least partially below the particulate matter feeder unit to receive particulate starter material dispensed from the feeder unit;
    an aqueous slurry discharging device in fluid communication with the mixing tank that permits discharge of the slurry after sufficient residence time within the mixing tank;
    a microprocessor to control the feeder drive assembly and the liquid flow control system;
    a pressurized water supply controlled by the liquid flow control system to supply water to the mixing tank; and
    a power supply connected to the feeder drive assembly, liquid flow control system, and microprocessor;
    wherein the particulate matter feeder unit comprises a dam and, a rotatable feeder cup having a single feed chamber disposed below the dam, and wherein the dam and feeder cup cooperate to control a flow of particulate matter downwardly through the feeder unit;
    wherein the mixing tank comprises a bottom having a first drain port and wherein the frame comprises a lower support plate having a second drain port that is in fluid communication with the first drain port;
    wherein the aqueous slurry discharging device comprises a rigid overflow drain tube having a lower end that provides a fluid-tight seal at the first drain port and having an upper end that is at least partially disposed in a substantially central location inside the mixing tank;
    wherein the upper end of the rigid overflow drain tube comprises at least one inlet port and at least two oppositely disposed scuppers.

2. Apparatus useful for feeding a particulate starter material comprising nutrient and bacteria to a mixing tank, for solubilizing the starter material inside the mixing tank, for promoting growth of the bacteria and for discharging an aqueous slurry comprising the bacteria from the mixing tank, the apparatus comprising:
    a housing having a frame and a releasable cover;
    a particulate matter feeder unit;
    a feeder drive assembly supported by the frame and releasably engaged with the particulate matter feeder unit to allow dispensing of particulate starter material;
    a liquid flow control system;
    a mixing tank disposed at least partially below the particulate matter feeder unit to receive particulate starter material dispensed from the feeder unit;
    an aqueous slurry discharging device in fluid communication with the mixing tank that permits discharge of the slurry after sufficient residence time within the mixing tank;
    a microprocessor to control the feeder drive assembly and the liquid flow control system;

a pressurized water supply controlled by the liquid flow control system to supply water to the mixing tank; and a power supply connected to the feeder drive assembly, liquid flow control system, and microprocessor;

wherein the particulate matter feeder unit comprises a feed canister, a base having an aperture, a dam having an aperture, and a rotatable feeder cup having a single feed chamber disposed below the dam, and wherein the dam and feeder cup cooperate to control a flow of particulate matter downwardly through the feeder unit; and wherein particulate starter material from the feed canister fills the feed chamber when it is in alignment with the aperture in the dam and out of alignment with the aperture in the base and wherein particulate starter material is dispensed to the mixing tank from the feed chamber when it is in alignment with the aperture in the base and out of alignment with the aperture in the dam; and wherein the rotatable feeder cup comprises surface enhancements that contact the aperture in the dam when the feed chamber is out of alignment with the aperture in the dam to reduce the likelihood of bridging or jamming of the particulate starter material passing from the feed canister to the feeder cup.

3. The apparatus of claim 2 wherein the particulate matter feeder unit is preloaded with particulate starter material and is slidably engageable with the drive assembly so that when the starter material is consumed, the particulate matter feeder unit may be disengaged from the drive assembly, removed from the dispensing apparatus, and replaced with another pre-loaded particulate matter feeder unit.

4. Apparatus useful for feeding a particulate starter material comprising nutrient and bacteria to a mixing tank, for solubilizing the starter material inside the mixing tank, for promoting growth of the bacteria and for discharging an aqueous slurry comprising the bacteria from the mixing tank, the apparatus comprising:

a housing having a frame and a releasable cover;

a particulate matter feeder unit;

a feeder drive assembly supported by the frame and releasably engaged with the particulate matter feeder unit to allow dispensing of particulate starter material;

a liquid flow control system;

a mixing tank disposed at least partially below the particulate matter feeder unit to receive particulate starter material dispensed from the feeder unit;

an aqueous slurry discharging device comprising a pipe in fluid communication with the mixing tank that permits discharge of the slurry after sufficient residence time within the mixing tank;

a microprocessor to control the feeder drive assembly and the liquid flow control system;

a pressurized water supply controlled by the liquid flow control system to supply water to the mixing tank;

scupper disposed near the upper end of the pipe; and a power supply connected to the feeder drive assembly, liquid flow control system, and microprocessor;

wherein the particulate matter feeder unit comprises a dam and a rotatable feeder cup having a single feed chamber disposed below the dam, and wherein the dam and feeder cup cooperate to control a flow of particulate matter downwardly through the feeder unit;

wherein the pipe is vertically disposed in a substantially central portion of the mixing tank, having a lower end in fluid communication with an aperture in a bottom surface of the mixing tank and an open upper end disposed at a desired level above the bottom surface of the mixing tank to permit the supply of a sufficient amount of water to grow bacteria from the particulate starter material before the water level reaches the upper end of the pipe to discharge the aqueous slurry.

5. Apparatus for dispensing an aqueous slurry comprising bacteria, the apparatus comprising:

a feeder unit comprising a feed canister, rotatable feeder cup, and a base releasably attached to the feed canister, the feed canister comprising solid walls and an open end and containing pre-loaded particulate starter material comprising bacteria, the base and rotatable feeder cup each comprising an aperture to dispense particulate starter material from the feed canister to a mixing tank, the mixing tank being at least partially disposed below the aperture in the base;

a feeder drive assembly releasably engaged with the feeder unit to rotate the aperture in the feeder cup into and out of alignment with the aperture in the base at predetermined intervals;

two or more liquid mixing jets disposed inside the mixing tank in substantially equidistant locations to supply liquid to the mixing tank;

an outlet for dispensing an aqueous slurry from the mixing tank, the aqueous slurry formed from particulate starter material and liquid combined in the mixing tank;

wherein the apparatus is configured to allow the feeder unit to be slidably disengaged from the feeder drive assembly without the use of tools and removed from the apparatus when the starter material has been consumed and to be replaced with another feeder unit pre-loaded with particulate starter material;

wherein the feeder drive assembly comprises a drive shaft and a plate that supports the base of the feeder unit; the aperture on the feeder unit base comprises a lip that engages with an aperture on the support plate; and wherein the base of the feeder unit further comprises a second aperture through which the drive shaft is disposed to provide rotational engagement with the rotatable feeder cup.

* * * * *